US006575958B1

(12) United States Patent
Happ et al.

(10) Patent No.: US 6,575,958 B1
(45) Date of Patent: Jun. 10, 2003

(54) CATHETER WITH IMPROVED TRANSITION

(75) Inventors: Dorrie M. Happ, San Jose, CA (US);
Jessica Liang, Redwood City, CA (US);
Chicheng Jack Wang, Sunnyvale, CA (US); Renee E. Garcia, Cupertino, CA (US); Rommel C. Lumauig, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/577,195

(22) Filed: May 23, 2000

(51) Int. Cl.⁷ ............................................. A61M 25/00
(52) U.S. Cl. .................. 604/525; 604/527; 604/96.01; 606/194
(58) Field of Search .................. 604/96.01, 264, 604/523, 524, 525, 526, 527; 606/192, 194

(56) References Cited

U.S. PATENT DOCUMENTS

| 5,300,025 A | 4/1994 | Wantink | 604/96 |
| 5,395,334 A * | 3/1995 | Keith et al. | 604/103.09 |
| 5,410,797 A | 5/1995 | Steinke et al. | 29/435 |
| 5,480,383 A | 1/1996 | Bagaoisan et al. | 604/96 |
| 5,833,706 A * | 11/1998 | St. Germain et al. | 604/96.01 |
| 5,891,110 A | 4/1999 | Larson et al. | 604/280 |
| 6,004,291 A * | 12/1999 | Ressemann et al. | 604/523 |
| 6,036,670 A * | 3/2000 | Wijeratne et al. | 604/526 |
| 6,193,686 B1 * | 2/2001 | Estrada et al. | 604/103.09 |

FOREIGN PATENT DOCUMENTS

| EP | 0 821 981 A2 | 8/1991 |
| EP | 0 925 801 A1 | 12/1997 |
| EP | 1 084 728 A1 | 9/2000 |
| WO | 99/24690 | 10/1999 |

* cited by examiner

Primary Examiner—Brian L. Casler
Assistant Examiner—Mark Han
(74) Attorney, Agent, or Firm—Fulwider Patton Lee & Utecht, LLP

(57) ABSTRACT

The invention is generally directed to an intraluminal catheter system with an improved transition between a proximal shaft portion and a more flexible distal shaft portion. The improvement provides enhanced flexibility and kink-resistance, thus, facilitating advancement through tortuous anatomy. The present catheters may be used for either or both angioplasty and stent deployment.

11 Claims, 9 Drawing Sheets

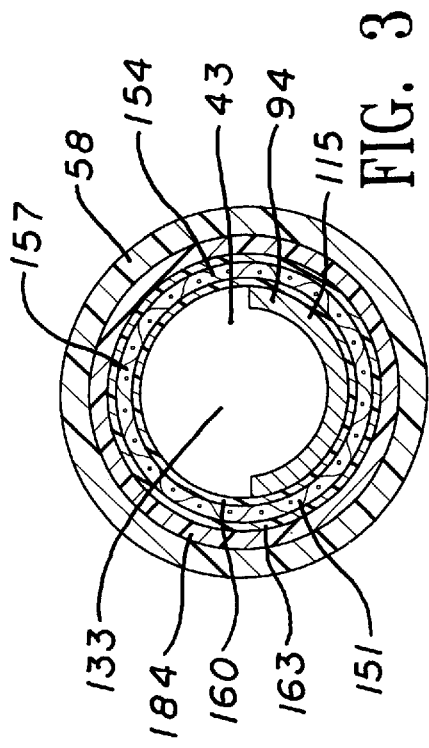
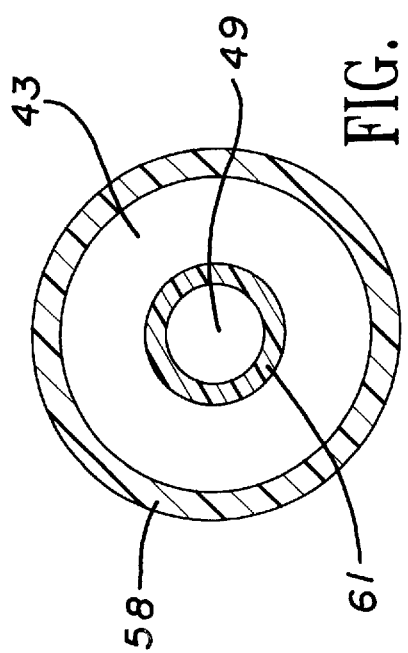
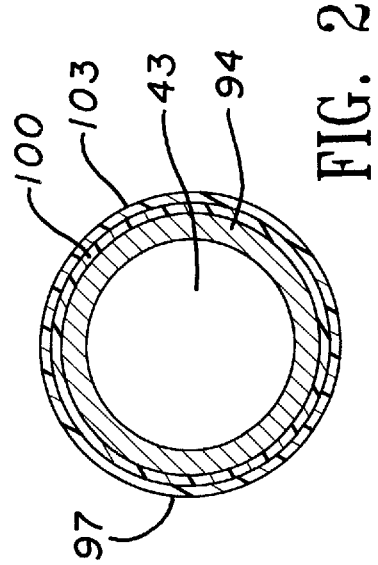
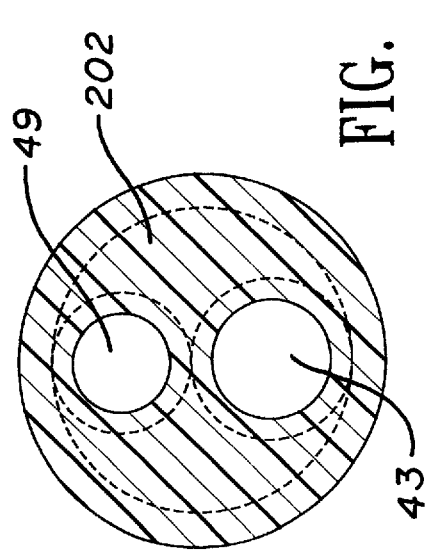

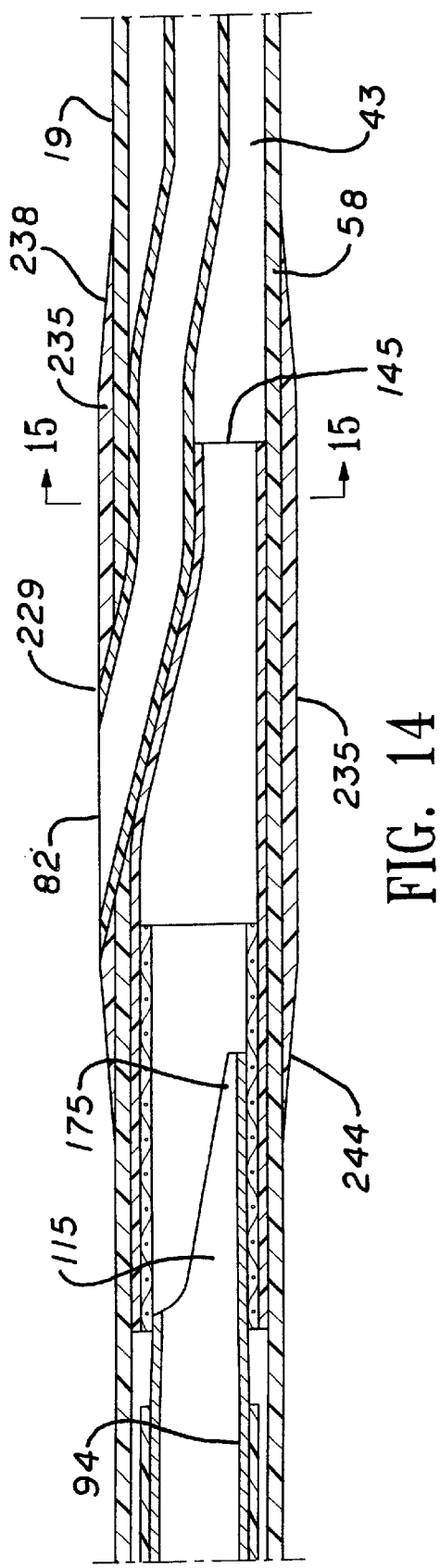
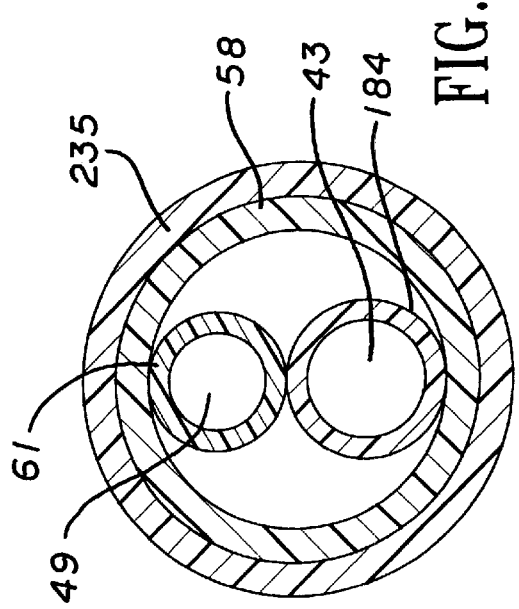

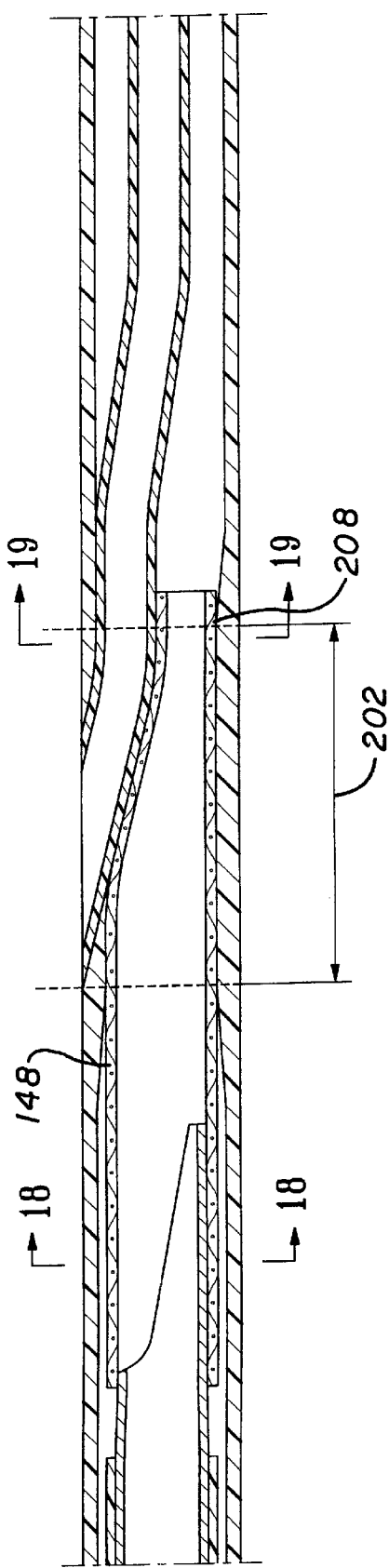
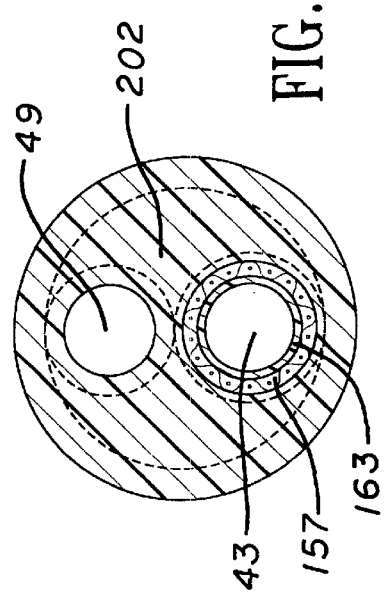
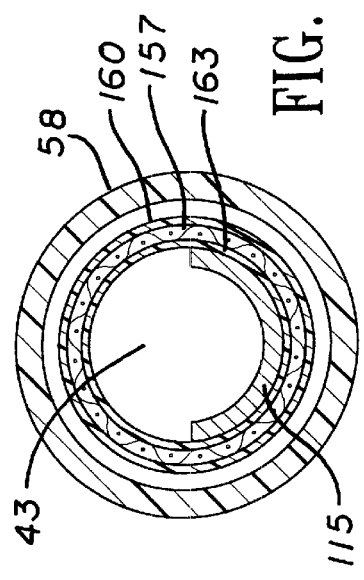

CATHETER WITH IMPROVED TRANSITION

FIELD OF INVENTION

The invention relates to the field of intravascular catheters, and particularly to a catheter suitable for angioplasty and/or stent deployment, and the like.

BACKGROUND OF THE INVENTION

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to keep open a stenosed vessel, and strengthen the dilated area by remaining inside the vessel. Instead of first using one catheter to dilate the body lumen and a second catheter to deploy the stent after the dilatation, the stent may be mounted on a balloon catheter and deployed at the same time the balloon is inflated to dilate the stenotic region.

Conventional balloon catheters for intravascular procedures, such as angioplasty and stent delivery, frequently have relatively stiff proximal shaft sections to facilitate advancement of the catheter within the patient's body lumen and a relatively flexible distal shaft sections to facilitate passage through tortuous anatomy such as distal coronary and neurological arteries without damage to the luminal wall. Typically, there is an intermediate shaft section or junction between the relatively stiff proximal shaft section and the relatively flexible distal shaft section which provides a transition between the proximal shaft section and less flexible than the distal shaft section.

A variety of intermediate shaft or junction designs have been utilized to provide a relatively smooth transition between the stiff proximal shaft section and the flexible distal shaft section. However, it has been difficult to develop a catheter design with an intermediate catheter shaft junction which provides a smooth transition and improved flexibility and which is also leak free when utilizing high pressure inflation fluid to inflate the balloon on the distal shaft section of the catheter for dilatation or stent deployment. Furthermore, they tend to kink when bent, into tight radius curves. The present invention satisfies these and other needs.

SUMMARY OF THE INVENTION

The invention is generally directed to an intraluminal catheter system with an improved transition between a proximal shaft portion and a more flexible distal shaft portion. The improvement provides enhanced flexibility and kink-resistance, thus, facilitating advancement through tortuous anatomy. The present catheters may be used for either or both angioplasty and stent deployment.

The improved flexibility allows the device to turn tight corners along the vasculature without applying large forces against the wall of the vessels, thus minimizing the surface friction between the catheter and the vessel. This allows more distal access. This optimization of flexibility may aggravate the kinking dynamic, as for example, bending stiffness discontinuities can be more pronounced as some softer catheter members are more likely to kink than stiffer members. Kinking of the catheter is also a common constraint to distal access. The kink creates a hinge point in the catheter so that the catheter can no longer navigate tight radius turns in the vasculature. Kinks often occur at the interface of two regions along the device having substantially different bending stiffness (i.e., have a discontinuity in the bending stiffness).

The kink resistance has been achieved by minimizing the differential in bending stiffness at the troublesome regions. The present invention includes various embodiments for minimizing the bending stiffness differential as well as increasing the overall flexibility of the catheter.

The catheter of the invention has an elongated proximal shaft section which transitions to a more flexible distal shaft section through an improved transition disposed between the proximal and distal shaft sections. An inflation lumen extends within the catheter shaft to a location spaced proximal to the distal end. An inner tubular member having a guidewire receiving lumen extends within at least the distal shaft section of the catheter. The proximal shaft section has proximal and distal ends and a portion of the inflation lumen extending therein. The distal tip of the proximal shaft section is preferably tapered distally to smaller transverse dimension. The distal shaft section has the inner tubular member extending within the distal shaft section to the port in the distal end thereof, and at least part of the inflation lumen extending within the distal shaft section to a location proximal to the distal end of the distal shaft section. An inflatable member such as a balloon is preferably provided on the distal shaft section which has an interior in fluid communication with the inflation lumen.

The transition includes a proximal portion of the distal shaft section and a distal portion of the proximal shaft section. At least a portion of the transition further includes, a tubular support member with an inner lumen extending therein, secured at a proximal end to the distal end of the proximal shaft section. Preferably, the tubular support member includes, a composite tubular member, which in turn, can include a tubular metallic member. The tubular metallic member includes at least one layer of metallic strand, in forms such as a metallic wound (or coil) or braid. Preferably, the composite tubular member includes polymeric inner and outer layers disposed on either side of the tubular metallic member.

In a preferred embodiment, the distal portion of the tubular support member further includes a tubular polymeric member having proximal and distal ends, with the proximal end extending proximal the distal end of the composite tubular member.

An intermediate portion of the tubular support member forms a junction 202, with the outer tubular member and the inner tubular member, the junction having a proximal end substantially being at the same longitudinal point as the outer tubular member aperture where the inner tubular member enters the outer tubular member, and is distally spaced apart from a distal end of the tubular support member. The junction may be formed by suitable adhesives, or mechanically connected by a suitable fastener or secured by a variety of other suitable means. The junction, preferably, is fusion bonded.

BRIEF DESCRIPTION OF THE DRAWINGS

FIG. 2 is a transverse cross sectional view of the catheter system of FIG. 1 taken along lines 2—2.

FIG. 3 is a transverse cross sectional view of the catheter system of FIG. 1 taken along lines 3—3.

FIG. 4 is a transverse cross sectional view of the catheter system of FIG. 1 taken along lines 4—4.

FIG. 5 is a transverse cross sectional view of the catheter system of FIG. 1 taken along lines 5—5.

FIG. 14 is schematic enlarged, longitudinal cross sectional view of an alternate embodiment showing a reinforcing sleeve disposed over a portion of the outer tubular member.

FIG. 15 is a transverse cross sectional view of the catheter system of FIG. 9 taken along lines 15—15.

FIG. 17 is schematic enlarged, longitudinal cross sectional view of an alternate embodiment showing the composite tubular member extending distally beyond a distal end of a junction.

FIG. 18 is a transverse cross sectional view of the catheter system of FIG. 17 taken along lines 18—18.

FIG. 19 is a transverse cross sectional view of the catheter system of FIG. 17 taken along lines 19—19.

DETAILED DESCRIPTION OF THE INVENTION

Figure 1:
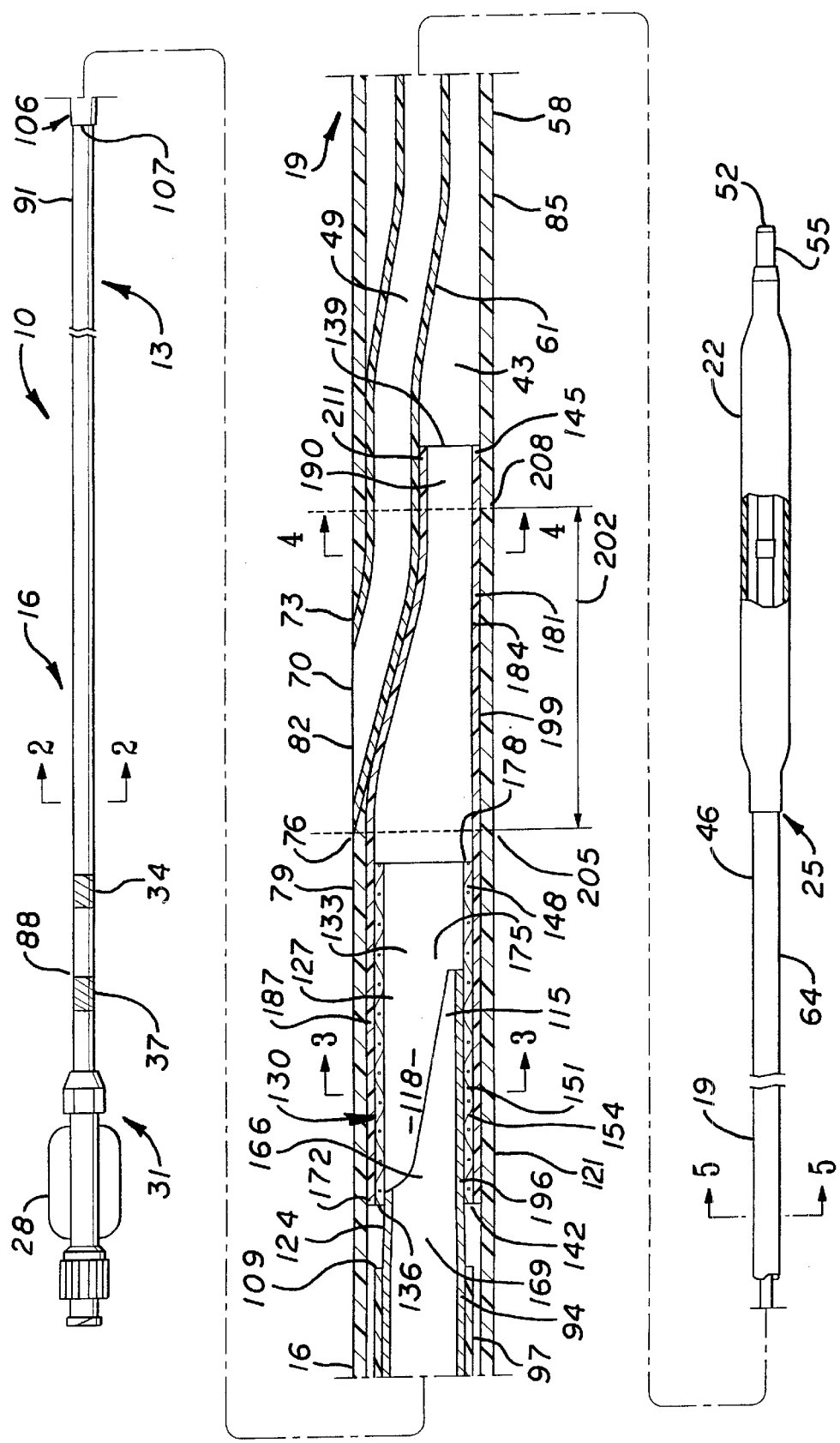
FIG. 1 is a schematic, elevational view partially in section, of the catheter system embodying features of the invention.

FIGS. 1 through 5 illustrates features of an intravascular catheter 10 embodying features of the invention which generally includes an elongated catheter shaft 13 with a proximal shaft section 16, a distal shaft section 19, and a radially expansive inflatable balloon 22 on a distal portion 25 of the distal shaft section 19. An adapter 28 is shown mounted on a proximal end 31, of proximal shaft section 16. Brachial and femoral radiopaque markers 34 and 37 are secured to an exterior 40 of the proximal shaft section 16 at a location distal to the adapter 28.

An inflation lumen 43 extends within the catheter shaft 13 from the proximal, end 31 thereof to a location spaced proximal to a distal end 46 of the shaft 13. A guidewire receiving lumen 49 extends within, at least, the distal shaft section 19 to a port 52 in a distal end 55 of the catheter 10.

The shaft 13, at the distal shaft section 19, includes an outer tubular member 58 and an inner tubular member 61 extending within a distal portion 64 of the distal shaft section 19 and defining the guidewire lumen 49 for receiving a guidewire (not shown) therein. The inflation lumen 43 and the guidewire receiving lumen 49 extend side-by-side along a substantial length of the distal shaft section 19. The inner tubular member 61 includes a port 70 at a proximal end 73 thereof exposed to an exterior 76 of a proximal portion 79 of the distal shaft section 19 at an aperture 82. In a preferred embodiment, the outer tubular member 58 is formed 6f a single piece tubular member 85.

The outer tubular member 58 may be formed of a polymeric material, including nylons and polyether block amides available under the trade name Pebax from Elf Atochem. The outer tubular member 58 is preferably formed at least in part of Nylon 12.

The inner tubular member 61 may be formed from a lubricious material such as high density polyethylene and, preferably, is of a tri-layer tubular construction including high density polyethylene as an inner layer, a copolymer of ethylene and acrylic acid such as Primacor from Dow Chemical Co. as a middle layer, and a nylon as the outer layer.

The proximal shaft section 16 has proximal and distal portions, 88 and 91, and includes a high strength hypotube 94 with an exterior polymeric jacket 97 having inner and outer layers, 100 and 103 respectively (see FIG. 2). The inflation lumen 43 within the proximal shaft section 16 is defined, at least in part, by the hypotube 94.

The hypotube 94 may be formed of a metallic material, and is preferably, formed of 304v stainless steel, NiTi alloy, MP35N, Elgiloy and the like. Non-metallic materials may also be used such as braided polyimide, and high strength polymers such as polyetheretherketone (PEEK), polyetherketone, and polyketone.

The exterior polymeric jacket 97 may be formed of any nylon, polyether block amides such as Pebax from Elf Atochem, copolymers of ethylene and acrylic acid such as Primacor from Dow Chemical Co., and polyolefins such as Plexar from Equistar Chemical Co., or any combination thereof. The exterior polymeric jacket 97 is preferably formed at least in part of nylon. Preferably, the jacket 97 has a two layered structure, the outer layer 103 being relatively lubricious to facilitate advancement of the catheter through the lumen of a guiding catheter, other lumens and ports, and the inner layer 100 being of high strength to withstand the pressures of the inflation fluid.

A proximal end 106 of the outer tubular member 58 is secured, preferably, by way of a laser fusion bond 107, to polymeric jacket 97 at a location proximal a distal end 109 of the polymeric jacket 97. Preferably, a distal end 112 of the bond 107 is spaced apart from the distal end 109 of the polymeric jacket 97, in a range from about 1.5 to about 2.5 cm, and the fusion 107 has a length of about 0.5 to about 2 mm.

A distal tip 115 of the hypotube 94 is tapered distally to a smaller transverse dimension. The hypotube tapered tip 115 is generally about 4 to about 8 cm long. In the embodiment described in FIG. 1, the hypotube tapered tip 115 is generally about 4 cm long.

A transition 118 including, at least a portion of, a proximal portion 121 of the distal shaft section 19 and a distal portion 124 of the proximal shaft section 16, provides for a smooth transition between the relatively rigid proximal shaft section 16 and the relatively flexible distal shaft section 19. At least a portion 127 of the transition 118 further includes, a tubular support member 130 with an inner lumen 133 extending therein between a proximal port 136 and a distal port 139 at proximal and distal ends, 142 and 145, respectively of the tubular support member 130. The tubular support member 130 is preferably formed from material and construction to provide the transition 118 with greater flexibility than the relatively more rigid proximal shaft section 16.

The length of the tubular support member 130 is generally about 5 cm to about 7 cm. Preferably, the tubular support member 130, as shown in FIG. 1, is about 6.7 cm. The tubular support member 130 has a wall thickness of about 0.004 to about 0.008 inches, preferably about 0.005 inches.

In a presently preferred embodiment, the tubular support member 130 includes, a composite tubular member 148, the composite tubular member 148, preferably, including a tubular metallic member 151 including a layer of metallic strand 154, in forms such as a metallic wound (or coil) or braid, such as braided metallic member 157 shown in FIGS. 1 and 3. Preferably, the composite tubular member 148 includes an inner layer 160 and an outer layer 163 disposed on either side of the tubular metallic member 151.

The tubular support member 130 may be formed of high strength polymeric materials which provide the transition 118 with greater flexibility than the relatively more rigid proximal shaft section 16. Suitable polymeric materials include engineering polymers such as polyetheretherketone (PEEK), polyetherketone, polyketone, polytetrafluoroethylene, or nylons. When the tubular support member 130 is a composite tubular member 148, including an inner layer 160 and an outer layer 163 disposed on either side of the tubular metallic member 151, the inner layer 160 is preferably formed of polytetrafluoroethylene, the outer layer 163 is preferably formed of nylon 6 or nylon CP and the tubular metallic member 151 is, preferably, formed of stainless steel.

The proximal end 142 of the tubular support member 130 is secured to a proximal end 166 of the tapered tip 115 of the hypotube 94. Preferably, the hypotube tapered tip 115 at its proximal end 166 includes a step 169 with the proximal end 142 of the tubular support member 130 extending proximally to a proximal end 172 of the step 169.

In a preferred embodiment, a distal end 175 of the tapered tip 115 of the hypotube 94 extends distally to a point proximal a distal end 178 of the composite tubular member 148.

In the presently preferred embodiment, shown in FIG. 1, a distal portion 181 of the tubular support member 130 further includes a tubular polymeric member 184 having proximal and distal ends 187 and 190, respectively. The tubular polymeric member 184 has a longitudinal dimension of about 1.2 cm. Tubular polymeric member 184 may, preferably, be formed of Nylon 12. Preferably, when a composite tubular member 148 having an outer layer 163 is present, the tubular polymer member 184 and the outer layer 163 are formed of compatible material, more preferably, of the same material, to facilitate adhesion to one another. However, the tubular polymeric member 184 may be formed of any material which can be easily bonded to the composite tubular member 148.

Figure 6:
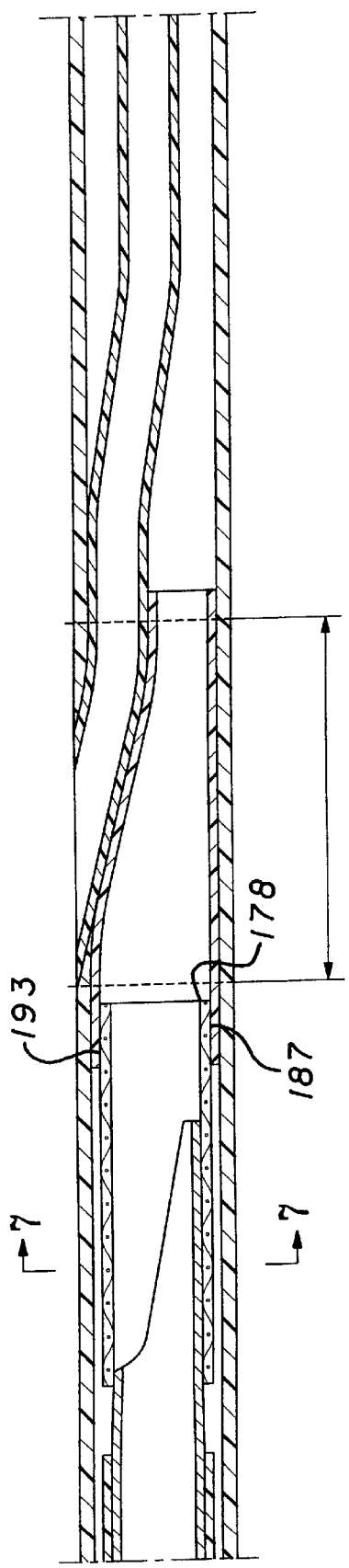
FIG. 6 is schematic enlarged, longitudinal cross sectional view of an alternate embodiment showing a proximal end of a tubular polymeric member forming a lapjoint with a distal end of a composite tubular member.
Figure 7:
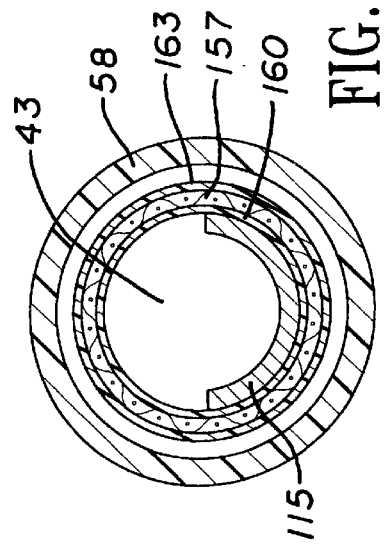
FIG. 7 is a transverse cross sectional view of the catheter system of FIG. 6 taken along lines 7—7.
Figure 8:
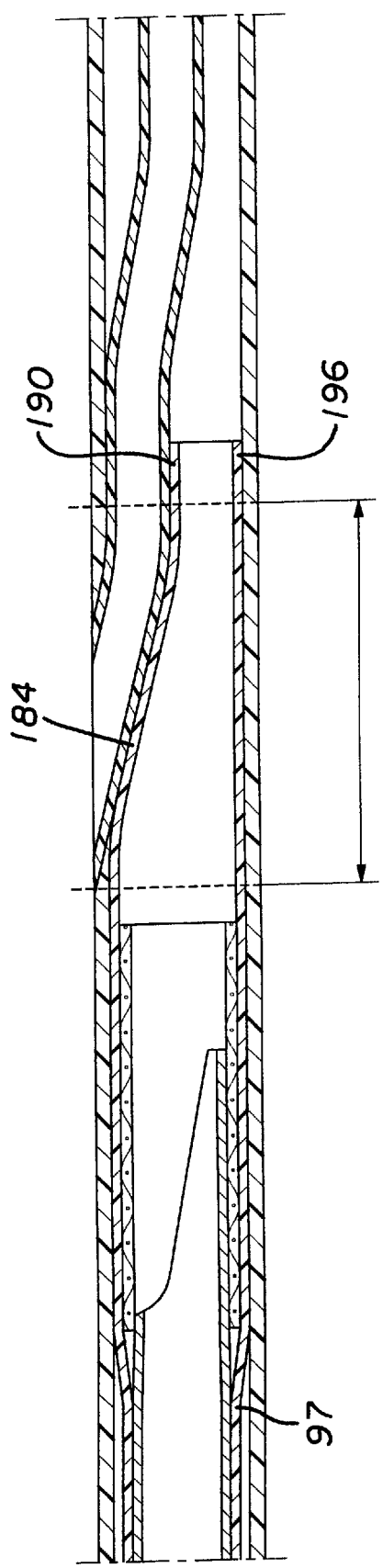
FIG. 8 is schematic enlarged, longitudinal cross sectional view of an alternate embodiment showing a distal end of a hypotube jacket extending distally beyond a distal end of a hypotube.

The proximal end 187 of the tubular polymeric member 184 extends over the distal end 178 of the composite tubular member 148 and over the composite tubular member 148 to a point proximal a distal end 196 of the hypotube 94. Alternatively, the proximal end 187 can extend over the distal end 178, forming a lapjoint 193, as shown in FIG. 6; or the proximal end 187 of the tubular polymeric member 184 can extend proximally to a point along the length of the composite tubular member 148 to the proximal end 142 of the step 169; or some point inbetween. In yet another embodiment, as shown in FIG. 8, the distal end 196 of the hypotube jacket 97 can extend distally to the same distal location as the distal end 190 of the tubular polymeric member 184.

An intermediate portion 199 of the tubular polymeric member 184 forms a junction 202, with the outer tubular member 58 and the inner tubular member 61, the junction 202 having a proximal end 205 substantially being at the same longitudinal point as the outer tubular member aperture 82 where the inner tubular member 61 enters the outer tubular member 58, and is distally spaced apart from a distal end 178 of the composite tubular member 148. The junction 202 has a distal end 208 proximal a distal end 211 of the tubular polymeric member 184. Preferably, the junction 202 has a longitudinal dimension ranging from 0.8 to about 1.2 cm, with the distal end 208 of the junction 202 spaced from the distal end 190 of the tubular polymeric member 184, by at least about 0.2 cm. The junction 202 may be formed by suitable adhesives such as Loctitie UV 3311, or mechanically connected by a suitable fastener or secured by a variety of other suitable means. The junction 202, preferably, is fusion bonded.

Figure 9:
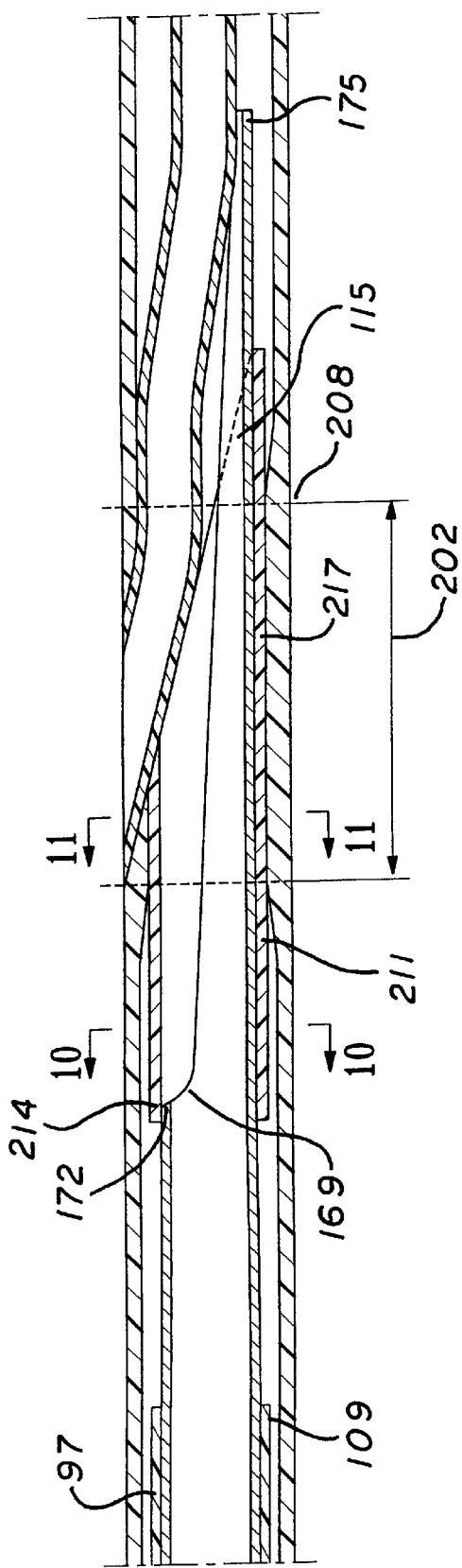
FIG. 9 is schematic enlarged, longitudinal cross sectional view of an alternate embodiment showing the distal end of the hypotube extending distally beyond a distal end of a junction.
Figure 11:
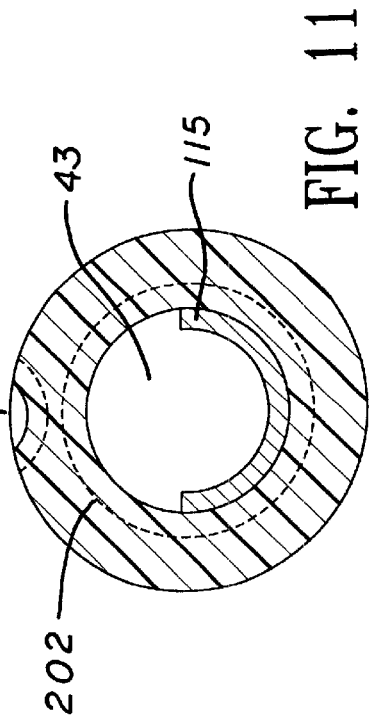
FIG. 11 is a transverse cross sectional view of the catheter system of FIG. 9 taken along lines 11—11.
Figure 10:
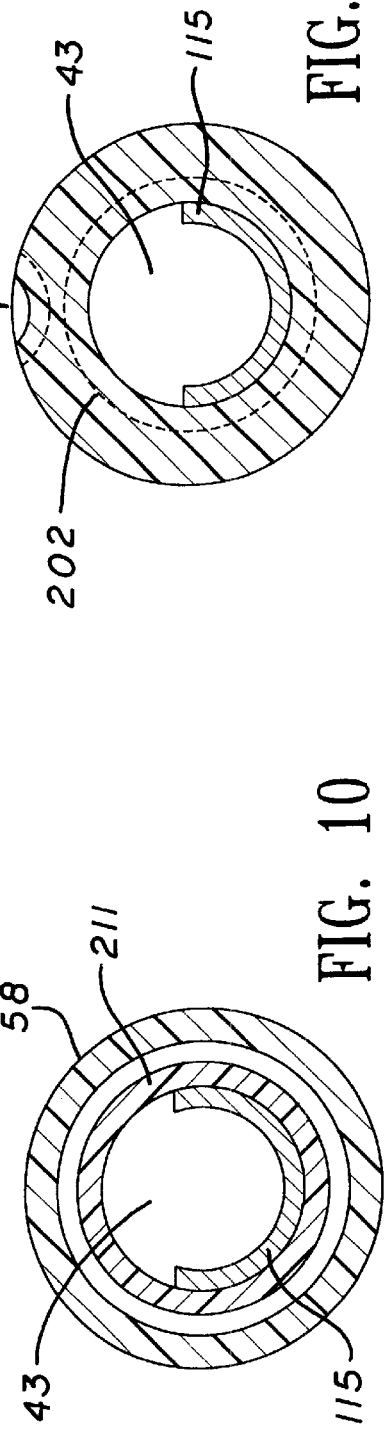
FIG. 10 is a transverse cross sectional view of the catheter system of FIG. 9 taken along lines 10—10.

In the embodiment illustrated in FIGS. 9–11, the distal end 175 of the hypotube tapered tip 115 extends distally beyond the distal end 208 of the junction 202. The hypotube tapered tip 115, preferably, has a longitudinal dimension of about 8 cm. Preferably, in this embodiment, the transitions 18 includes a polymeric tubular member 211' having proximal and distal ends, 214 and 217. The proximal end 214 can extend to the proximal end 172 of the step 169, or alternatively, can extend proximally, to a point proximal to the distal end 109 of the hypotube jacket 97 with the distal end 217 extending into the fused junction area 202. Preferably, the polymeric tubular member 211, has a length of about 5.7 cm, and a wall thickness of about 0.008 inches at the proximal end 214 to about 0.004 inches at the distal end 217.

The polymeric tubular member 211 may beformed of any suitable material, preferably, polyetheretherketone. The transverse cross-section of the polymeric tubular member 211 distal end 217 can have the cross-section of a general or truncated cylinder, as shown.

Figure 12:
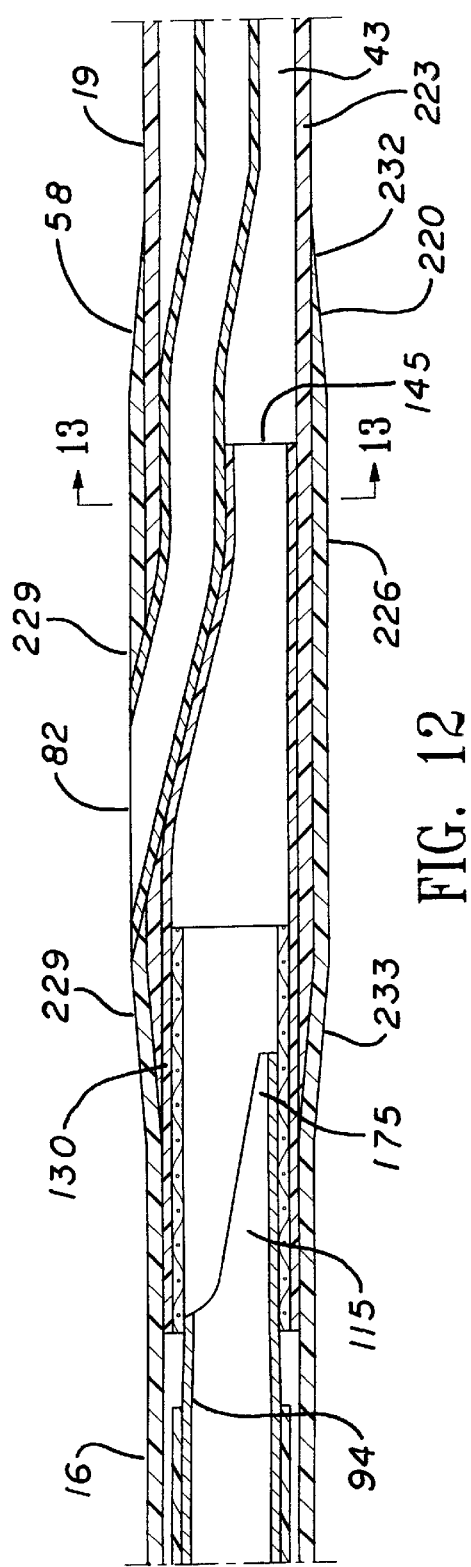
FIG. 12 is schematic enlarged, longitudinal cross sectional view of an alternate embodiment showing an outer tubular member including proximal and distal outer tubular members.
Figure 13:
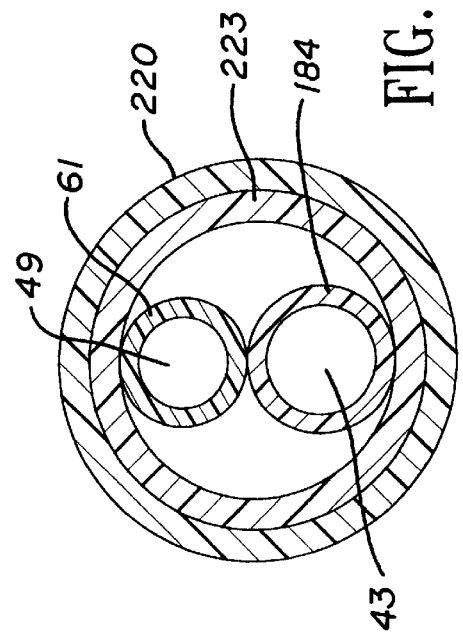
FIG. 13 is a transverse cross sectional view of the catheter system of FIG. 12 taken along lines 13—13.

Now turning to FIGS. 12 and, 13, the outer tubular member 58 includes proximal and distal outer tubular members, 220 and 223, forming a lapjoint 226 which includes an area 229 along the distal shaft section 19 immediately to either side of the distal shaft section aperture 82. Preferably, a distal end 232 of the lapjoint 226 extends distal to the distal end 145 of the tubular support member 130, with a proximal end 233 of the lapjoint 226 extending proximally at least to a point at the distal end 175 of the hypotube 94 tapered tip 115. The proximal and distal outer tubular members, 220 and 223, may be formed individually and thereafter joined to one another, or can be co-extruded with each other. Although in the embodiment shown in FIGS. 14–15, the junction 202 is not present, the catheter 10 may be formed so as to include the junction 202.

The proximal and distal outer members, 220 and 223, are formed of material compatible to form a bond therebetween. Preferably, the proximal outer member 220 is formed of a nylon such as Nylon 12 and the distal outer member 223 is formed of a soft, flexible material such as a softer nylon or a polyether block amide such as Pebax 72D.

In yet another embodiment, features of which are illustrated in FIGS. 14 and 15, a reinforcing sleeve 235 is disposed over a portion of the outer tubular member 58, in aperture overlap area 229 along the distal shaft section 19 immediately to either side of the distal shaft section aperture 82. Preferably, a distal end 238 of the reinforcing sleeve 235 extends distal to the distal end 145 of the tubular support member 130, with a proximal end 244 of the reinforcing sleeve 235 extending proximally at least to a point at the distal end 175 of the hypotube 94, tapered tip 115. Preferably, the reinforcing sleeve 235 is formed of material such as Nylon, and has a longitudinal dimension of about 4 cm.

Figure 16:
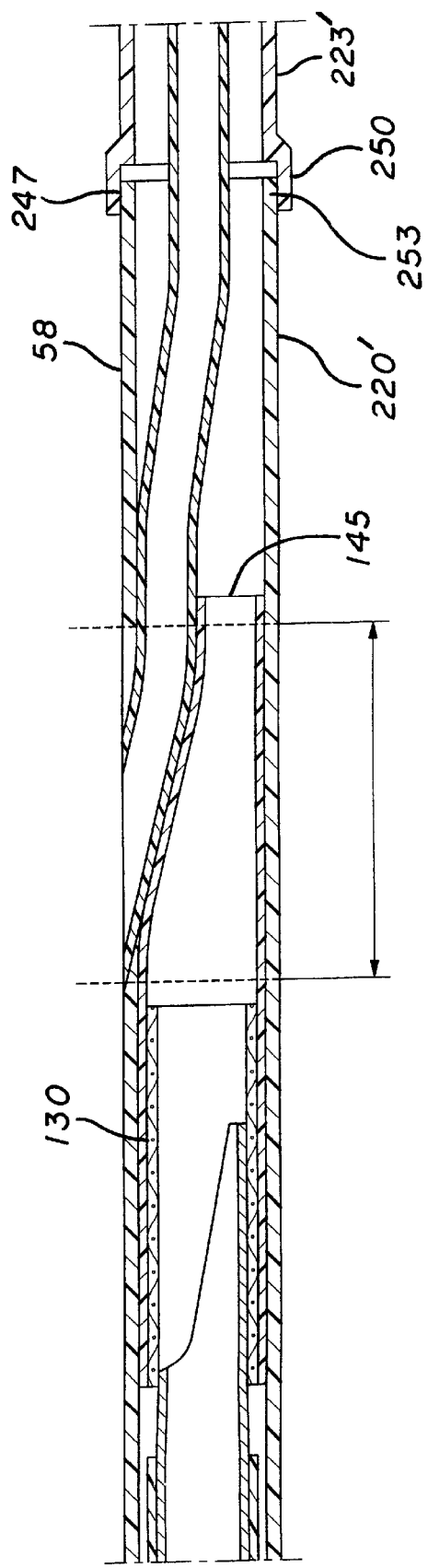
FIG. 16 is schematic enlarged, longitudinal cross sectional view of an alternate embodiment showing outer tubular member including proximal and distal outer tubular members with a distal end of the proximal outer tubular member extending distal to a distal end of an inflation lumen.

In yet another embodiment, features of which are illustrated in FIG. 16, the outer tubular member 58 includes proximal and distal outer tubular members, 220' and 223', with a distal end 247 of the proximal outer tubular member 220' extending distal to the distal end 145 of the tubular support member 130. A proximal end 250 of the distal outer tubular member 223' forms an overlap joint 253 over the distal end 247 of the proximal outer tubular member 220'. Preferably, the overlap 253 has a longitudinal dimension of about 4 cm.

In yet another embodiment, as shown in FIGS. 17–19, the composite tubular member 148 extends distally beyond the distal end 208 of the junction 202, preferably by about 0.2 cm.

The balloon 22 may be formed of suitable compliant, non-compliant, or hybrid compliant material, including thermoplastic and thermosetting polymers depending upon the end use, e.g. dilatation, stent delivery etc. The presently preferred balloon polymeric material is a relatively compliant polyether block amide such as Pebax 70 sold by Elf Atochem. Other materials include Nylon 11 and 12 and Pebax 72. Compliant polymeric materials, i.e. compliant within the working expansion of the balloon, which provide a wingless balloon and which have substantially elastic recoil during deflation are also suitable for stent delivery work. Other desirable polymeric materials for balloon manufacture include polyurethanes such as TECOTHANE.

The catheter shaft 13 will generally have the dimensions of conventional dilatation or stent deploying catheters. The length of the catheter 10, measured from the distal end of the adapter 16 to the distal end 46 of the catheter shaft 13 may be about 90 cm to about 150 cm, and is typically about 137 cm. The outer tubular member 58 of the distal shaft section 19 has a length of about 15 cm to about 25 cm, typically about 20 cm, an outer diameter (OD) of about 0.025 in to about 0.045 in, preferably about 0.034–0.038 in and an inner diameter (ID) of about 0.02 to about 0.04, preferably about 0.028 to about 0.032 in. The inner tubular member 61 has a length of about 18 cm to about 40 cm, preferably about 25 to about 30 cm, an OD of about 0.02 to about 0.026 in and an ID of about 0.012 to about 0.022 in. The inner and outer tubular members, 58 and 61, may taper in the distal section to a smaller OD or ID.

The length of the balloon 22 may be about 10 mm to about 50 mm, preferably about 10 mm to about 40 mm. In an expanded state, the balloon diameter is generally about 0.5 mm to about 4.5 mm, typically about 1.5 to about 4 mm. The wall thickness will vary depending upon the burst pressure requirements and the hoop strength of the balloon material.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. An intravascular catheter, comprising:
   an elongated catheter shaft having proximal and distal ends, and a proximal and a distal shaft section, each shaft section having proximal and distal ends;
   an inflation lumen extending within at least a portion of the catheter shaft from an inflation lumen proximal end to a location spaced proximal to the distal end of the catheter shaft;
   a guidewire receiving lumen extending within at least the distal shaft section to a port in the distal end thereof;
   an inflatable member on the distal shaft section and having an interior in fluid communication with the inflation lumen; and
   a tubular support member positioned so as to engage an interior surface of said distal shaft section near the proximal end of the distal shaft section and an exterior surface of said proximal shaft section, wherein said support member includes a tubular reinforcing section that is shorter than said tubular support member and wherein the distal end of said proximal shaft section is received in said tubular reinforcing section.

2. The intravascular catheter of claim 1, wherein said tubular reinforcing section comprises a metallic component.

3. The intravascular catheter of claim 2, wherein said metallic component is disposed between an inner and outer polymeric layer.

4. The intravascular catheter of claim 2, wherein said metallic component comprises coiled strand.

5. The intravascular catheter of claim 2, wherein said metallic component comprises braided strand.

6. The intravascular catheter of claim 1, wherein said tubular support member includes a tubular polymeric member having a proximal end, wherein said tubular reinforcing section has a proximal end and wherein said proximal end of said polymeric member and said proximal end of said tubular reinforcing section are aligned with one another.

7. The intravascular catheter of claim 1, wherein said tubular support member includes a tubular polymeric member having a proximal end, wherein said tubular reinforcing section has a proximal end and wherein said proximal end of said polymeric member is distal to said proximal end of said tubular reinforcing section.

8. The intravascular catheter of claim 1, wherein said tubular support member includes a tubular polymeric member having a proximal end, wherein said tubular reinforcing section has a proximal end and wherein said proximal end of said polymeric member is proximal to said proximal end of said tubular reinforcing section.

9. The intravascular catheter of claim 1, wherein said tubular support member includes a tubular polymeric member having a distal end, wherein said tubular reinforcing section has a distal end and wherein said distal end of said polymeric member is distal to said distal end of said tubular reinforcing section.

10. The intravascular catheter of claim 9, wherein guidewire lumen extends to a proximal port in said distal shaft section wherein said proximal port is proximal to said distal end of said polymeric tubular member.

11. The intravascular catheter of claim 1, further comprising a reinforcing sleeve disposed about an exterior surface of said distal shaft section wherein at least a portion thereof overlaps at least a portion of said tubular support member.

* * * * *

UNITED STATES PATENT AND TRADEMARK OFFICE
CERTIFICATE OF CORRECTION

PATENT NO. : 6,575,958 B1
DATED : June 10, 2003
INVENTOR(S) : Dorrie M. Happ et al.

It is certified that error appears in the above-identified patent and that said Letters Patent is hereby corrected as shown below:

Column 6,
Line 32, after "148" (first occurrence), delete "and over the composite tubular member 148".

Signed and Sealed this

Twenty-first Day of October, 2003

JAMES E. ROGAN
*Director of the United States Patent and Trademark Office*